(12) United States Patent
Harigae et al.

(10) Patent No.: US 12,428,387 B2
(45) Date of Patent: Sep. 30, 2025

(54) METHOD FOR PRODUCING COMPOUND

(71) Applicant: Kureha Corporation, Tokyo (JP)

(72) Inventors: Ryo Harigae, Tokyo (JP); Chiemi Kojima, Tokyo (JP); Shingo Konno, Tokyo (JP); Toru Yamazaki, Tokyo (JP)

(73) Assignee: Kureha Corporation, Tokyo (JP)

(*) Notice: Subject to any disclaimer, the term of this patent is extended or adjusted under 35 U.S.C. 154(b) by 482 days.

(21) Appl. No.: 18/040,365

(22) PCT Filed: Aug. 6, 2021

(86) PCT No.: PCT/JP2021/029343
§ 371 (c)(1),
(2) Date: Feb. 2, 2023

(87) PCT Pub. No.: WO2022/030622
PCT Pub. Date: Feb. 10, 2022

(65) Prior Publication Data
US 2023/0271929 A1    Aug. 31, 2023

(30) Foreign Application Priority Data
Aug. 6, 2020  (JP) ................................ 2020-134138

(51) Int. Cl.
 *C07D 301/02* (2006.01)
 *C07C 67/42* (2006.01)
 *C07D 249/08* (2006.01)
 *C07D 303/48* (2006.01)

(52) U.S. Cl.
 CPC .......... *C07D 301/02* (2013.01); *C07C 67/42* (2013.01); *C07D 249/08* (2013.01); *C07D 303/48* (2013.01)

(58) Field of Classification Search
 CPC ... C07D 301/02; C07D 249/08; C07D 303/48
 See application file for complete search history.

(56) References Cited

U.S. PATENT DOCUMENTS

| | | |
|---|---|---|
| 4,533,659 A | 8/1985 | Eckhardt et al. |
| 4,886,892 A | 12/1989 | Zerbes et al. |
| 10,053,436 B2 | 8/2018 | Gebhardt et al. |
| 10,358,426 B2 | 7/2019 | Dietz et al. |
| 10,897,897 B2 | 1/2021 | Gewehr et al. |
| 10,945,434 B2 | 3/2021 | Harigae et al. |
| 2007/0066669 A1 | 3/2007 | Mauler-Machnik et al. |
| 2008/0269263 A1 | 10/2008 | Dahmen et al. |
| 2012/0088660 A1 | 4/2012 | Renner et al. |
| 2012/0108422 A1 | 5/2012 | Renner et al. |
| 2013/0096299 A1 | 4/2013 | Kusano et al. |
| 2014/0155262 A1 | 6/2014 | Dietz et al. |
| 2014/0296535 A1 | 10/2014 | Kanno |
| 2015/0051231 A1 | 2/2015 | Borges et al. |
| 2015/0218134 A1 | 8/2015 | Masano et al. |
| 2015/0313225 A1 | 11/2015 | Lohmann et al. |
| 2015/0344445 A1 | 12/2015 | Lohmann et al. |
| 2016/0227772 A1 | 8/2016 | Gewehr et al. |
| 2017/0081296 A1 | 3/2017 | Dietz et al. |
| 2017/0166540 A1 | 6/2017 | Gebhardt et al. |
| 2018/0199569 A1 | 7/2018 | Gewehr et al. |
| 2020/0288714 A1* | 9/2020 | Harigae .............. C07D 401/06 |
| 2021/0186016 A1 | 6/2021 | Gewehr et al. |

FOREIGN PATENT DOCUMENTS

| | | |
|---|---|---|
| AU | 2018365928 B2 | 2/2020 |
| CA | 3071569 A1 | 5/2019 |
| CL | 2020000546 A1 | 7/2020 |
| CN | 102491959 A | 6/2012 |
| CN | 103059004 A | 4/2013 |
| CN | 103649057 A | 3/2014 |
| CN | 103930417 A | 7/2014 |
| CN | 104540818 A | 4/2015 |
| CN | 105050406 A | 11/2015 |
| CN | 111032631 A | 4/2020 |
| CO | 2020002329 A2 | 4/2020 |
| EA | 202090456 A2 | 7/2020 |
| EP | 0096660 A1 | 12/1983 |
| EP | 0099165 A1 | 1/1984 |
| EP | 0619812 A1 | 10/1994 |
| EP | 2731935 B1 | 3/2016 |

(Continued)

OTHER PUBLICATIONS

Office Action for IN202317005660, dated Nov. 2, 2023, 6 pages.
Restriction Requirement for U.S. Appl. No. 17/594,373, dated Sep. 21, 2022, 8 pages.
Atkinson, David C., et al., "Substituted (2-Phenoxyphenyl) Acetic Acids with Antiinflammatory Activity", Journal of Medicinal Chemistry, 1983, vol. 25, No. 10, 8 pages.
Extended European Search Report for European Patent Application No. 18876885.7, 11 pages.
Office Action from Colombian Patent Application No. NC2020/0002329 dated Nov. 24, 2020, 15 pages.
Office Action from Mexican Patent Application No. MX/a/2020/002380 dated Jan. 12, 2021, 9 pages.

(Continued)

*Primary Examiner* — Matthew P Coughlin
(74) *Attorney, Agent, or Firm* — Abel Schillinger, LLP

(57) ABSTRACT

A method by which an intermediate product of an azole derivative can be produced at a lower cost than known production methods is provided. A method for producing a compound represented by General Formula (IV) includes converting a compound represented by General Formula (II) into the compound represented by General Formula (IV) using (a) dimethyl sulfide and/or dimethyl sulfoxide, and (b) a methyl-LG (an LG is a nucleophilically substitutable leaving group and is selected from the group consisting of a halogen group, an alkoxysulfonyloxy group, an aryloxysulfonyloxy group, an alkylsulfonyloxy group, a haloalkylsulfonyloxy group, and an arylsulfonyloxy group) in the presence of an inorganic base.

5 Claims, 1 Drawing Sheet

(56) References Cited

FOREIGN PATENT DOCUMENTS

| EP | 3712135 A1 | 9/2020 |
|---|---|---|
| EP | 3957177 A1 | 2/2022 |
| JP | S58170770 A | 10/1983 |
| JP | S5931766 A | 2/1984 |
| JP | 59-206375 A | 11/1984 |
| JP | 2012-530109 A | 11/2012 |
| JP | 2012-530110 A | 11/2012 |
| JP | 2014520832 A | 8/2014 |
| JP | 2016535007 A | 11/2016 |
| JP | 2019048845 A | 3/2019 |
| WO | 9311118 A1 | 6/1993 |
| WO | 2011136268 A1 | 11/2011 |
| WO | 2012125533 A1 | 9/2012 |
| WO | 2013007767 A1 | 1/2013 |
| WO | 2013144105 A1 | 10/2013 |
| WO | 2014082871 A1 | 6/2014 |
| WO | 2014082881 A1 | 6/2014 |
| WO | 2014095548 A1 | 6/2014 |
| WO | 2014095672 A1 | 6/2014 |
| WO | 2014095994 A1 | 6/2014 |
| WO | 2015055755 A1 | 4/2015 |
| WO | 2015185708 A1 | 12/2015 |
| WO | 2016/005211 A1 | 1/2016 |
| WO | 2017029179 A1 | 2/2017 |
| WO | 2018145921 A1 | 8/2018 |
| WO | 2019/093522 A1 | 5/2019 |
| WO | 2020213739 A1 | 10/2020 |
| WO | 2021170830 A1 | 9/2021 |

OTHER PUBLICATIONS

Office Action from Ukrainian Patent Application No. a202000480 dated Feb. 17, 2021, 5 pages. NOTE: The Ukrainian examiner confirmed that D4, WO2013/007776A1, was typed incorrectly in the attached Ukrainian Office Action. It should have been typed as WO2013/007767A1.
Office Action from Chilean Patent Application No. 00546-2020 dated Mar. 4, 2021, with translation, 33 pages.
Office Action for PH Application No. 1-2020-550075, dated Nov. 11, 2022, with translation, 4 pages.
Office Action for MX Application No. MX/a/2020/002380, dated Jul. 2, 2021, with translation, 6 pages.
Office Action for EP Application No. 18876885.7, dated Jun. 30, 2022, 4 pages.
Office Action for EP Application No. 18876885.7, dated Jan. 11, 2022, 4 pages.
Office Action for EP Application No. 18876885.7, dated Jun. 23, 2021, 5 pages.
Office Action for EA Application No. 202090456, dated Oct. 5, 2021, with translation, 4 pages.
Office Action for EA Application No. 202090456, dated Mar. 26, 2021, with translation, 6 pages.
Office Action for CL Application No. 00546-2020, dated Jul. 9, 2021, with translation, 6 pages.
Office Action for BR Application No. BR112020002160-1, dated Sep. 20, 2022, with translation, 6 pages.
Office Action for CO Application No. NC2021/0015225, dated Feb. 21, 2023, 9 pages.
English translation of Office Action for CO Application No. NC2021/0015225, dated Feb. 21, 2023, 9 pages.
Office Action for PH Application No. 1-2021-552560, dated Mar. 13, 2023, 6 pages.
Office Action for EP Application No. 20791025.8, dated Mar. 22, 2023, 9 pages.
Office Action for PH Application No. 1-2020-550075, dated Apr. 3, 2023, 4 pages.
Office Action for CR Application No. 2020-0103, dated Apr. 28, 2023, 9 pages.
English translation of the Office Action for CR Application No. 2020-0103, dated Apr. 28, 2023, 6 pages.
Office Action for UA Application No. A202106007, dated May 3, 2023, 5 pages.
English translation of the Office Action for UA Application No. A202106007, dated May 3, 2023, 6 pages.
Non-Final Office Action for U.S. Appl. No. 17/594,373, dated Jun. 7, 2023, 50 pages.
Hearing Notice for IN Application No. 202017003921, dated Aug. 3, 2023, 2 pages.
Office Action for PH Application No. 1-2020-550075, dated Aug. 11, 2023, 4 pages.
Office Action for EP Application No. 20791025.8, dated Sep. 7, 2023, 4 pages.
Hearing Notice for IN Application No. 202117048015, dated Sep. 6, 2023, 3 pages.
Non-Final Office Action for U.S. Appl. No. 17/594,373, dated Oct. 20, 2023, 34 pages.
Plant Disease: Pathogens and Cycles [online]. CropWatch, 2019 [retrieved on Oct. 15, 2023]. Retrieved from the internet: <https://web.archive.org/web/20191018181244/https://cropwatch.unl.edu/soybean-management/plant-desease>. (Year: 2019).
Emami et al. Current Medicinal Chemistry vol. 30, pp. 220-249. (Year: 2023).
Office Action for NZ781580, dated Oct. 18, 2023, 3 pages.
Office Action for NZ781580, dated Nov. 27, 2023, 3 pages.
Final Office Action for U.S. Appl. No. 17/594,373, dated Jan. 23, 2024, 32 pages.
Non-Final Office Action for U.S. Appl. No. 16/636,502, dated Jul. 21, 2020, 34 pages.
Office Action for CN202180060304.5, dated Jan. 15, 2024, 6 pages.
English Translation of the Office Action for CN202180060304.5, dated Jan. 15, 2024, 7 pages.
Non-Final Office Action for U.S. Appl. No. 17/594,373, dated Feb. 16, 2023, 65 pages.
Office Action for CA Application No. 3135695, dated Nov. 18, 2022, 3 pages.
Extended European Search Report for International Application No. PCT/JP2020/016993, dated Apr. 28, 2022.
Office Action for AU2020257751, dated Nov. 25, 2021.
Office Action for CN202080027996.9, dated Oct. 21, 2022, 4 pages.
English translation of Office Action for CN202080027996.9, dated Oct. 21, 2022, 7 pages.
The Eurasian Patent Organization (EAPO) Date of mailing: Jan. 13, 2022; Application No. 202192756; Eurasian Patent Attorney: Mrs. Nosyreva E. L., Notification.
Canadian Office Action for Application No. 3135695, dated Apr. 27, 2022.
International Preliminary Report on Patentability for PCT/JP2020/016993, dated Oct. 28, 2021.
EA Office Action for Application No. 202192756/28, dated May 31, 2022.
International Search Report for International Application No. PCT/JP2020/016993 dated Jun. 16, 2020.
Translation of the International Search Report for International Application No. PCT/JP2020/016993 dated Jun. 16, 2020.
Written Opinion for International Application No. PCT/JP2020/016993 dated Jun. 16, 2020.
Translation of the Written Opinion for International Application No. PCT/JP2020/016993 dated Jun. 16, 2020.
Chinese Office Action issued for Chinese Application No. 2020800279969, dated May 17, 2022.
Office Action for Korean Patent Application No. 10-2021-7037146, dated Feb. 14, 2022.
Office Action for CO Application No. NC2021/0015225, dated Nov. 9, 2022, 8 pages.
English translation of Office Action for CO Application No. NC2021/0015225, dated Nov. 9, 2022, 13 pages.
Office Action for Indian Application No. 202117048015, dated Mar. 4, 2022.
Office Action for CN Application No. 202080027996.9, dated Feb. 9, 2023, 4 pages.
English translation of Office Action for CN Application No. 202080027996.9, dated Feb. 9, 2023, 6 pages.

(56) References Cited

OTHER PUBLICATIONS

Office Action for CL Application No. 202102743, dated Feb. 14, 2023, 15 pages.
English translation of Office Action for CL Application No. 202102743, dated Feb. 14, 2023, 12 pages.
Non-Final Office Action for U.S. Appl. No. 16/636,502, now U.S. Pat. No. 10,945,434, dated Jul. 21, 2020, 34 p. .
Guo, S. et al., "Metal-free oxidative esterification of acetophenones with alcohols: a facile one-pot approach to α-ketoesters," RSC Advances, published on Oct. 11, 2016, vol. 6, No. 100, retrieved on Nov. 22, 2019, pp. 98422-98426.
Yang, L. et al., "Synthesis of Pelorol and Analogues: Activators of the Inositol 5-Phosphatase SHIP," Organic Letters, published on Feb. 16, 2005, vol. 7, No. 6, pp. 1073-1076.
International Search Report of the International Searching Authority for PCT/JP2018/041971 with mailing date of Jan. 15, 2019.
English translation of International Search Report of the International Searching Authority for PCT/JP2018/041971 with mailing date of Jan. 15, 2019.
Written Opinion of the International Preliminary Examining Authority of PCT/JP2018/041971 with mailing date of Jan. 15, 2019.
English translation of Written Opinion of the International Preliminary Examining Authority of PCT/JP2018/041971 with mailing date of Jan. 15, 2019.
Notification of Reasons for Refusal of the Intellectual Property Office of Japan for JP 2019-552425 with mailing date of Apr. 7, 2020.
English translation of Notification of Reasons for Refusal of the Intellectual Property Office of Japan for JP 2019-552425 with mailing date of Apr. 7, 2020.
Office Action of the Intellectual Property Office of Canada for CA 3,071,569 with mailing date of Apr. 6, 2020.
Translation of the International Preliminary Report on Patentability (Chapter 1) for PCT/JP2018/041971 with issue date of May 19, 2020.
Notification of Reason for Refusal of the Intellectual Property Office of Korea for KR 10-2020-7002610 with mailing date of May 1, 2020.
English translation of Notification of Reason for Refusal of the Intellectual Property Office of Korea for KR 10-2020-7002610 with mailing date of May 1, 2020.
Search Report of the Intellectual Property Office of China for CN 201880050458.4 with search date of Jun. 3, 2020.
Office Action of the Intellectual Property Office of China for CN 201880050458.4 with mailing date of Jun. 11, 2020.
English translation of Search Report of the Intellectual Property Office of China for CN 201880050458.4 with search date of Jun. 3, 2020.
English translation of Office Action of the Intellectual Property Office of China for CN 201880050458.4 with mailing date of Jun. 11, 2020.
Examination Report of the Intellectual Property Office of India for IN 202017003921 with mailing date of Jun. 11, 2020.
Office Action of the Intellectual Property Office of Eurasian Patent Organization for EA 202090456 with mailing date of Jun. 11, 2020.
English translation of Office Action of the Intellectual Property Office of Eurasian Patent Organization for EA 202090456 with mailing date of Jun. 11, 2020.
Partial Supplementary European Search Report for European Patent Application 18876885.7 dated Aug. 6, 2020, 11 pages.
Yu-Xiu Liu, et al., "Design, synthesis and acaricidal/insecticidal activities of etoxazole analogues", New Journal of Chemistry, vol. 37, No. 6, Jan. 1, 2013, pp. 1803-1810, XP055717562.
Xiuling Yu, et al., "Design, synthesis and acaricidal/insecticidal . . ."; Journal of Agricultural and Food Chemistry, 2016, vol. 64(15), pp. 3034-3040.
Office Action from Chilean Patent Application No. 2020-00546 dated Nov. 9, 2020, 33 pages.
Office Action from Eurasian Patent Application No. 202090456, dated Nov. 20, 2020, 4 pages.
Office Action from Chinese Patent Application No. 201880050458. 4, dated Nov. 13, 2020, 17 pages.
Office Action from IL273066, mailed Sep. 29, 2020, 6 pages.
Office Action for BR112020002160-1, dated Feb. 26, 2024, 5 pages.
Translation of Office Action for BR1120200021601, dated Feb. 26, 2024, 5 pages.
Extended European Search Report for EP21853755.3, mailed Jul. 16, 2024, 5 pages.
Office Action for CR20200103, dated Oct. 8, 2024, 7 pages.
English translation of Office Action for CR20200103, dated Oct. 8, 2024, 7 pages.
Raghunadh, et al., "An Efficient and Practical Synthesis of Aryl and Hetaryl a-Keto Esters", Technology Development Centre, Custom Pharmaceutical Services, Dr. Reddy's Laboratories Ltd., Miyapur. Hyderabad. 500 049, India; Received Jul. 14, 2011; revised Nov. 3, 2011.
Son, et al., "High Potency Phenylquinoxalinone Cystic Fibrosis Transmembrane Conductance Regulator (CFTR) Activators", Department of Chemistry, University of California, Davis, California 95616, United States, Feb. 23, 2017.
Kambale, et al., "Lewis acid catalyzed cascade annulation of alkynols with a-ketoesters: a facile access to y-spiroketal-y-lactones", Chem Commun, 2017; 53, 6641.
Office Action for U.S. Appl. No. 17/594,373, dated May 8, 2024, 32 pages.
English translation of the International Preliminary Report on Patentability for PCT Application No. PCT/JP2021/029343, mailed Feb. 16, 2023, 6 pages.
Office Action for CR20200103, dated Jul. 8, 2025, 7 pages.
English translation of Office Action for CR20200103, dated Jul. 8, 2025, 7 pages.

* cited by examiner

[FIG. 1]
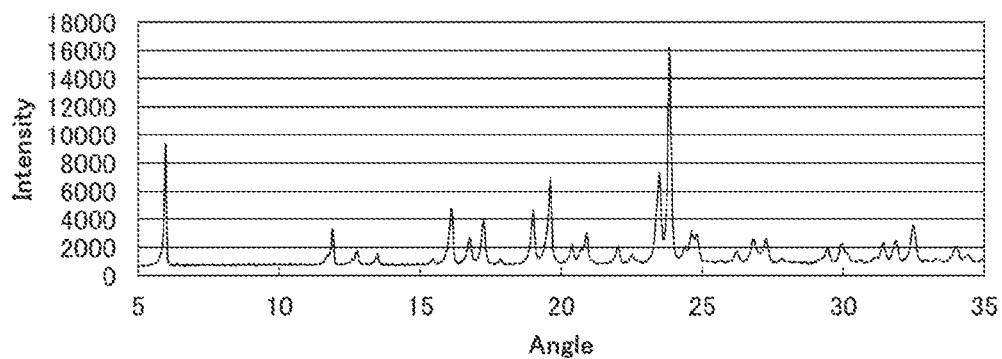
[FIG. 2]
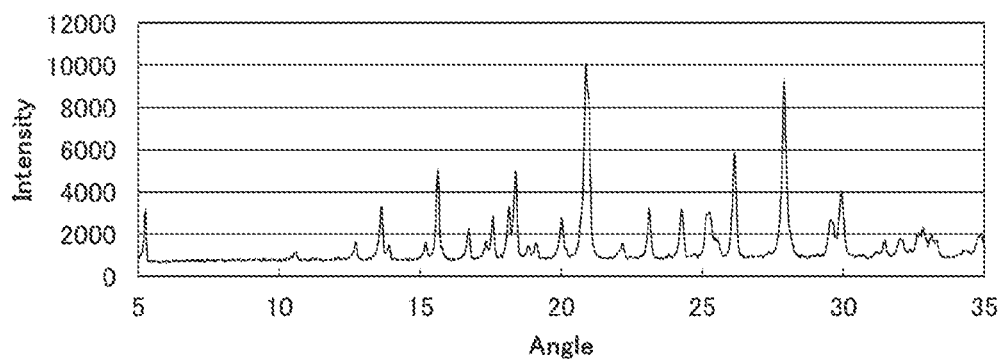
[FIG. 3]
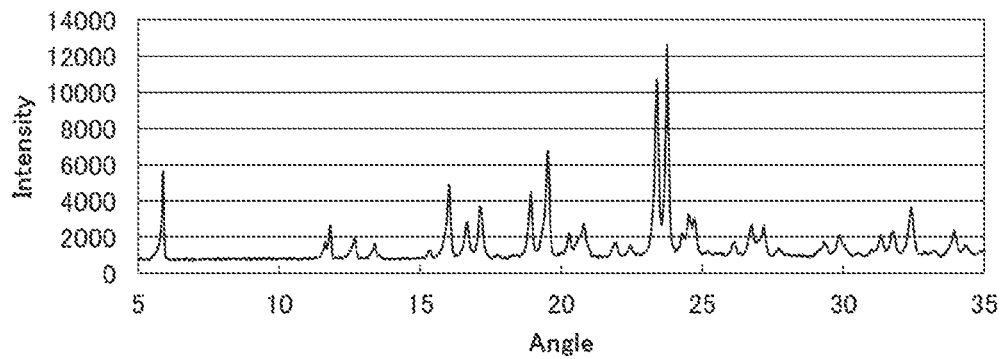

METHOD FOR PRODUCING COMPOUND

TECHNICAL FIELD

The present invention relates to a method for producing a compound.

BACKGROUND ART

An azole derivative is useful as an agricultural or horticultural chemical exhibiting a high controlling effect. To produce an azole derivative, a method for producing an intermediate product of an azole derivative has been studied. For example, Patent Document 1 describes a method for producing methyl-2-(2-chloro-4-(4-chlorophenoxy)phenyl)-2-oxoacetate, which is an intermediate product of an azole derivative.

CITATION LIST

Patent Literature

Patent Document 1: WO 2019/093522 A1

SUMMARY OF INVENTION

Technical Problem

The method for producing an intermediate compound of an azole derivative described in Patent Document 1 describes performing oxiranation using trimethylsulfoxonium bromide (TMSOB) and substituting a ketone group for a ketoester group using iodine or iodomethane. However, since TMSOB, iodine, and iodomethane are expensive, there is an issue of increased production cost of an intermediate product of an azole derivative. Therefore, a method for producing an intermediate product of an azole derivative at a lower cost is demanded.

The present invention has been completed in light of the issues described above, and an object of an aspect of the present invention is to realize a method by which an intermediate product of an azole derivative can be produced at a lower cost than those of known production methods.

Solution to Problem

To solve the issues described above, the production method according to an aspect of the present invention is a method for producing a compound represented by General Formula (IV):

[Chem. 1]

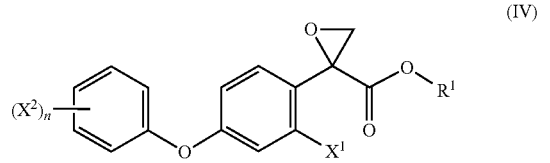

where in Formula (IV), $R^1$ is a $C_1$-$C_6$-alkyl group;
$X^1$ is a halogen group, a $C_1$-$C_4$-haloalkyl group, or a $C_1$-$C_4$-haloalkoxy group;
$X^2$ is a halogen group, a $C_1$-$C_4$-haloalkyl group, or a $C_1$-$C_4$-haloalkoxy group; and
n is 1, 2, or 3.

The method includes converting a compound represented by General Formula (II) into the compound represented by General Formula (IV) using:
(a) dimethyl sulfide and/or dimethyl sulfoxide, and
(b) a methyl-LG (an LG is a nucleophilically substitutable leaving group and is selected from the group consisting of a halogen group, an alkoxysulfonyloxy group, an aryloxysulfonyloxy group, an alkylsulfonyloxy group, a haloalkylsulfonyloxy group, and an arylsulfonyloxy group) in the presence of an inorganic base:

[Chem. 2]

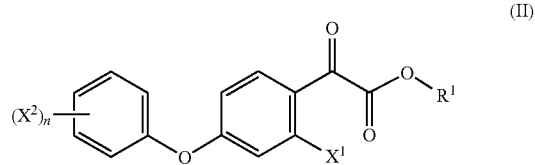

where in Formula (II), $R^1$, $X^1$, $X^2$, and n are respectively the same as $R^1$, $X^1$, $X^2$, and n in Formula (IV).

Advantageous Effects of Invention

According to an aspect of the present invention, an intermediate product of an azole derivative can be produced at a lower cost than those of known production methods.

BRIEF DESCRIPTION OF THE DRAWINGS

FIG. 1 is an X-ray diffraction pattern of triazol-1-yl (A). Intensity indicates X-ray diffraction intensity, and angle indicates a diffraction angle (2θ).

FIG. 2 is an X-ray diffraction pattern of triazol-4-yl (B). Intensity indicates X-ray diffraction intensity, and angle indicates a diffraction angle (2θ).

FIG. 3 is an X-ray diffraction pattern of a mixture (C) having triazol-1-yl:triazol-4-yl of 95:5, synthesized in the present examples. Intensity indicates X-ray diffraction intensity, and angle indicates a diffraction angle (2θ).

DESCRIPTION OF EMBODIMENTS

A preferred embodiment for carrying out the present invention will now be explained. Note that the embodiment explained below illustrates a representative embodiment of the present invention, and it should not be interpreted that the scope of the present invention is narrowed by this embodiment.

1. Method For Producing Compound Represented by General Formula (IV)

The method for producing a compound represented by General Formula (IV) (hereinafter, referred to as "oxirane derivative (IV)") according to an aspect of the present invention (hereinafter, referred to as "production method 1") will be described:

[Chem. 3]

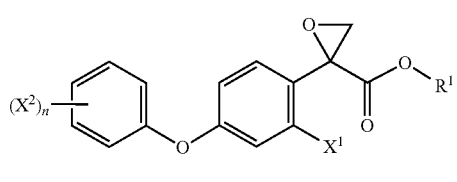

(IV)

where in Formula (IV), $R^1$ is a $C_1$-$C_6$-alkyl group;

$X^1$ is a halogen group, a $C_1$-$C_4$-haloalkyl group, or a $C_1$-$C_4$-haloalkoxy group;

$X^2$ is a halogen group, a $C_1$-$C_4$-haloalkyl group, or a $C_1$-$C_4$-haloalkoxy group; and n is 1, 2, or 3.

The $C_1$-$C_6$-alkyl group is a linear or branched alkyl group having from 1 to 6 carbon atoms, and examples thereof include a methyl group, an ethyl group, a 1-methylethyl group, a 1,1-dimethylethyl group, a propyl group, a 1-methylpropyl group, a 2-methylpropyl group, a 1,1-dimethylpropyl group, a 2,2-dimethylpropyl group, a 1-ethylpropyl group, a butyl group, a 1-methylbutyl group, a 2-methylbutyl group, a 3-methylbutyl group, a 3,3-dimethylbutyl group, a 2,2-dimethylbutyl group, a 1,1-dimethylbutyl group, a 1-ethylbutyl group, a 2-ethylbutyl group, a pentyl group, a 1-methylpentyl group, a 2-methylpentyl group, a 3-methylpentyl group, and a 4-methylpentyl group.

Examples of the halogen group include a chlorine group, a bromine group, an iodine group, and a fluorine group.

The $C_1$-$C_4$-haloalkyl group has one or more halogen atoms as substituents at substitutable positions of the $C_1$-$C_4$-alkyl group, and in a case of substitution with two or more halogen groups, the halogen groups may be the same or different. Note that the $C_1$-$C_4$-alkyl group is a linear or branched alkyl group having from 1 to 4 carbon atoms.

The $C_1$-$C_4$-alkyl group is a linear or branched alkyl group having from 1 to 4 carbon atoms, and examples thereof include a methyl group, an ethyl group, a propyl group, and a butyl group. The halogen group is as described above. Examples of the $C_1$-$C_4$-haloalkyl group include a chloromethyl group, a 2-chloroethyl group, a 2,3-dichloropropyl group, a bromomethyl group, a chlorodifluoromethyl group, a trifluoromethyl group, and a 3,3,3-trifluoropropyl group.

The $C_1$-$C_4$-haloalkoxy group has one or more halogen atoms as substituents at substitutable positions of the $C_1$-$C_4$-alkoxy group, and in a case of substitution with two or more halogen groups, the halogen groups may be the same or different. Note that the $C_1$-$C_4$-alkoxy group is a linear or branched alkoxy group having from 1 to 4 carbon atoms.

The $C_1$-$C_4$-alkoxy group is a linear or branched alkoxy group having from 1 to 4 carbon atoms, and examples thereof include a methoxy group, an ethoxy group, a propoxy group, an isopropoxy group, a 1-methylpropoxy group, a 2-methylpropoxy group, a butoxy group, and a 1,1-dimethylethoxy group.

The production method 1 of the present aspect include converting a compound represented by General Formula (II) (hereinafter, referred to as "ketoester derivative (II)") into an oxirane derivative (IV) according to Scheme 1 below (hereinafter, referred to as "Step 1"). Note that $R^1$, $X^1$, $X^2$, and n in the following Scheme 1 correspond to $R^1$, $X^1$, $X^2$, and n in General Formula (IV) above.

Scheme 1

[Chem. 4]

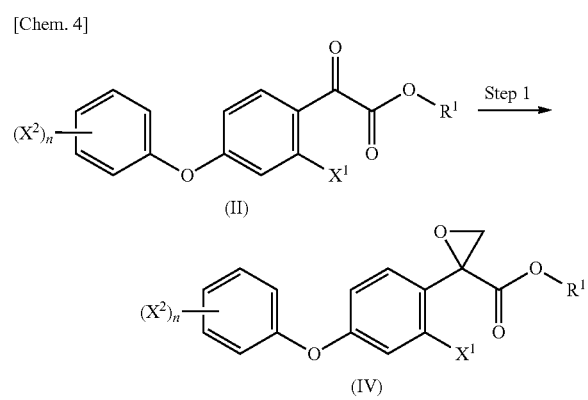

Step 1

Step 1 in the production method 1 of the present aspect is a step of converting a ketoester derivative (II) into an oxirane derivative (IV) using:

(a) dimethyl sulfide and/or dimethyl sulfoxide; and (b) a methyl-LG (an LG is a nucleophilically substitutable leaving group and is selected from the group consisting of a halogen group, an alkoxysulfonyloxy group, an aryloxysulfonyloxy group, an alkylsulfonyloxy group, a haloalkylsulfonyloxy group, and an arylsulfonyloxy group) in the presence of an inorganic base:

[Chem. 5]

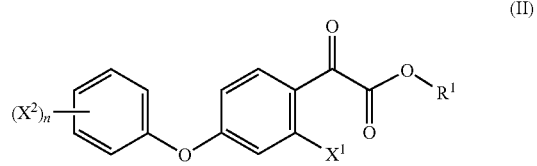

(II)

where in Formula (II), $R^1$, $X^1$, $X^2$, and n are respectively the same as $R^1$, $X^1$, $X^2$, and n in Formula (IV).

In Step 1, oxiranation is performed by using dimethyl sulfide and/or dimethyl sulfoxide and a methyl-LG while a sulfonium salt is prepared in a reaction system. That is, the preparation of the sulfonium salt and the oxiranation reaction are performed simultaneously.

The inorganic base is added from the perspective of proceeding the reaction of Step 1. Examples of the inorganic base used in Step 1 include sodium hydride, cesium carbonate, potassium phosphate, and potassium carbonate, and potassium carbonate is preferred.

LG is a nucleophilically substitutable leaving group, such as a leaving group selected from the group consisting of a halogen group, an alkoxysulfonyloxy group, an aryloxysulfonyloxy group, an alkylsulfonyloxy group, a haloalkylsulfonyloxy group, and an arylsulfonyloxy group, and is preferably an alkoxysulfonyloxy group.

The amount of the inorganic base coexisted in the reaction system in Step 1 is preferably from 1.0 to 10.0 equivalents (eq.) with respect to 1 equivalent (eq.) of the ketoester derivative (II) from the perspective of proceeding the reaction of Step 1.

The amount of "(a) dimethyl sulfide and/or dimethyl sulfoxide" described above to be added to the reaction system in Step 1 (referred to as "amount required for reaction") is preferably from 1.0 to 10.0 equivalents (eq.) with respect to 1 equivalent (eq.) of the ketoester derivative (II) from the perspective of adequately performing the reaction.

The amount of "(b) methyl-LG" described above to be added to the reaction system in Step 1 (referred to as "amount required for reaction") is preferably from 1.0 to 10.0 equivalents (eq.) with respect to 1 equivalent (eq.) of the ketoester derivative (II) from the perspective of adequately performing the reaction.

Step 1 proceeds in an organic solvent. As the organic solvent, a solvent proceeding the reaction of Step 1 is appropriately selected, and examples of the organic solvent include dichloroethane. The reaction of Step 1 can be performed, for example, in an oil bath while heating to reflux and stirring are performed. At this time, the oil bath temperature is, for example, may be set to be 85 to 100° C. in a manner that the internal temperature becomes 80 to 90° C.

In the production method 1 of the present aspect, in Step 1, the amounts required for reaction of the (a) and the (b) are preferably divided and added in multiple batches. The divided addition in Step 1 refers to addition performed by dividing the amounts required for reaction of the (a) and the (b) into one or more batches. The timing of adding the second or later additions and the number of divided addition can be appropriately set to appropriate timing and number by a person skilled in the art, taking reaction conditions and the like into consideration. For example, the performance of second divided addition is only required before activity of the reagent added in the first time is lost. By the divided addition of the (a) and the (b), effect of reducing the used amount of reagents of the (a) and the (b) required for the reaction of Step 1 is achieved, compared to a case where the (a) and the (b) are added in one batch without divided addition. It is conceived that this is because the reaction is performed more efficiently by the divided addition of the (a) and the (b) compared to a case where the (a) and the (b) are added in one batch.

As long as all the amounts required for reaction are added to the reaction system, the addition amounts for one addition (referred to as "divided addition amount") is not particularly limited. The divided addition amount can be appropriately adjusted depending on the number of divided addition. Furthermore, divided addition amounts (e.g., when the amounts required for reaction are divided into two and added, divided addition amounts for the first addition and the second addition) may be the same or different.

The (a) may be dimethyl sulfide and/or dimethyl sulfoxide, and is preferably both dimethyl sulfide and dimethyl sulfoxide. In the (a), by adding a combination of dimethyl sulfide and dimethyl sulfoxide, effect of improving yield can be achieved as well as reducing used amounts of reagents compared to a case where only dimethyl sulfoxide is added.

In the production method 1 of the present aspect, because oxiranation is performed by using dimethyl sulfide and/or dimethyl sulfoxide and a methyl-LG, which are relatively easy to obtain, are used in place of TMSOB, separate preparation of TMSOB is not needed. By performing the production method 1 of the present aspect, for example, construction costs for a plant needed to produce TMSOB and labor costs and utility costs during production are not needed. Also, for an operator of the production method 1 of the present aspect, there are advantages during production, such as shortening of batch cycle time required for production of TMSOB. Furthermore, because an operator of the production method 1 of the present aspect handles DMSO in a basic condition, there is an advantage of high safety during production.

The oxirane derivative (IV) produced in the production method 1 of the present aspect is an intermediate product of a compound represented by General Formula (I) below (hereinafter, referred to as "azole derivative (I)"). The production method 1 of the present aspect can produce the azole derivative (I) at a low cost because the production method 1 can produce the oxirane derivative (IV) at a low cost without using expensive TMSOB, iodine, and iodomethane:

[Chem. 6]

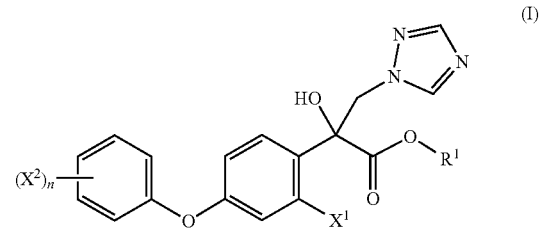

where in Formula (I), $R^1$, $X^1$, $X^2$, and n are respectively the same as $R^1$, $X^1$, $X^2$, and n in General Formula (IV) above.

2. Method For Producing Ketoester Derivative (II)

The production method 1 of the present aspect may include a method for producing a ketoester derivative (II) of the present aspect (hereinafter, referred to as "production method 2") before Step 1.

The production method 2 of the present aspect include converting a compound represented by General Formula (III) (hereinafter, referred to as "methyl ketone derivative (III)") into a ketoester derivative (II) according to Scheme 2 below (hereinafter, referred to as "Step 2"). Note that $R^1$, $X^1$, $X^2$, and n in the following Scheme 2 correspond to $R^1$, $X^1$, $X^2$, and n in General Formula (IV) above.

Scheme 2

[Chem. 7]

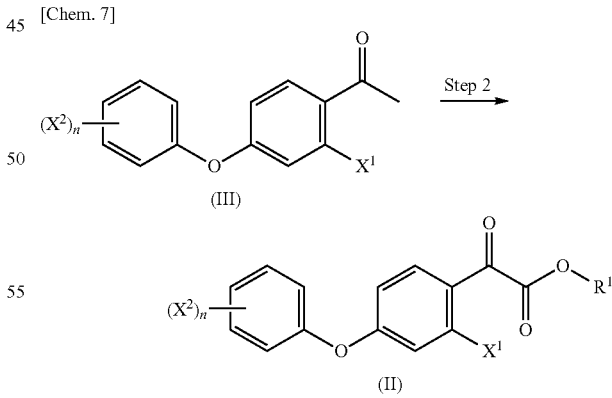

Step 2

In Step 2 in the production method 2 of the present aspect, in a solvent containing dimethyl sulfoxide, bromine is allowed to react with a methyl ketone derivative (III) while the reaction system is heated, and subsequently $R^1$—OH ($R^1$ is the same as $R^1$ in General Formula (IV) above) is allowed to react, and thus a ketoester derivative (II) is formed:

[Chem. 8]

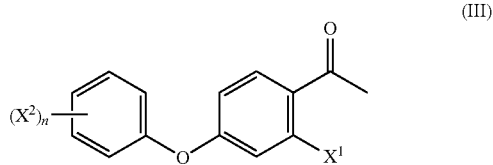

(III)

where in Formula (III), $X^1$, $X^2$, and n are respectively the same as $X^1$, $X^2$, and n in Formula (IV).

In Step 2, synthesis of ketocarboxylic acid using bromine and dimethyl sulfoxide and esterification using $R^1$—OH are performed continuously. By using a bromine in synthesis reaction of a ketocarboxylic acid, compared to a case where iodine is used like Patent Document 1, the ketoester derivative (II) can be produced at a lower cost in a higher yield. Furthermore, because the $R^1$—OH is used as an esterification reagent used in the esterification reaction, compared to a case where iodomethane is used like Patent Document 1, the ketoester derivative (II) can be produced at a lower cost.

The amount of dimethyl sulfoxide added to the reaction system in Step 2 is preferably from 2.0 to 10.0 equivalents (eq.) with respect to 1 equivalent (eq.) of the methyl ketone derivative (III) from the perspective of adequately performing the reaction.

The amount of bromine added to the reaction system in Step 2 is preferably from 0.5 to 3.0 equivalents (eq.) with respect to 1 equivalent (eq.) of the methyl ketone derivative (III) from the perspective of adequately performing the reaction.

For the reaction temperature of the synthesis reaction of the ketocarboxylic acid in Step 2, the internal temperature is preferably from 60 to 85° C., and more preferably at 70° C., from the perspective of suitably performing the reaction. For example, the synthesis reaction of the ketocarboxylic acid in Step 2 can be performed in an oil bath while stirring and heating are performed to set the internal temperature the temperature described above. Furthermore, the esterification reaction in Step 2 can be performed, for example, in an oil bath while heating is performed to reflux. At this time, to make the internal temperature preferably from 55 to 65° C., and more preferably at 65° C., the oil bath temperature may be set to be from 60 to 80° C.

Step 2 proceeds in an organic solvent. As the organic solvent, a solvent proceeding the reaction of Step 2 is appropriately selected, and examples of the organic solvent include dichloroethane.

In Step 2 in the production method 2 of another aspect of the present invention, in the solvent containing dimethyl sulfoxide, after heating the reaction system to which bromine is added, the bromine may be allowed to react with a methyl ketone derivative (III) while the methyl ketone derivative (III) is added, and subsequently $R^1$—OH ($R^1$ is the same as $R^1$ in General Formula (IV) above) may be allowed to react, and thus a ketoester derivative (II) may be formed.

In a case where the methyl ketone derivative (III) is added after the reaction system to which the bromine is added is heated, the heating temperature of the reaction system before addition of the methyl ketone derivative (III) is a temperature that makes the internal temperature preferably from 60 to 75° C., and more preferably at 65° C. Furthermore, the reaction temperature of the reaction system after the methyl ketone derivative (III) addition is a temperature that makes the internal temperature preferably from 65 to 80° C., and more preferably at 70° C. By addition of the methyl ketone derivative (III) after the reaction system to which the bromine is added is heated, heat build-up during synthesis reaction of the ketocarboxylic acid can be suppressed, and thus Step 2 can proceed more safely.

Furthermore, in the production method 2 according to another aspect, Step 2 is preferably performed in the presence of at least one type of compound selected from the group consisting of urea, adipic acid dihydrazide, and dibutylhydroxytoluene, and more preferably performed in the presence of urea. In Step 2, white accretion is generated inside the reactor due to use of the bromine. This white accretion is not included in the end product of Step 2; however, because the white accretion can cause clogging in the reactor, the white accretion in the reactor needs to be removed often. However, by performing the reaction of Step 2 in the presence of the compound described above, generation of the white accretion attached inside the reactor in Step 2 can be suppressed. As a result, the production efficiency is improved because the removal treatment of the white accretion inside the reactor is not necessary, which is advantageous for an operator. From the perspective of high effect of suppressing generation of white accretion, the compound that is allowed to coexist in the reaction system in Step 2 is preferably urea.

The amount of at least one type of compound selected from the group consisting of urea, adipic acid dihydrazide, and dibutylhydroxytoluene, which coexists in the reaction system in Step 2, is preferably from 0.1 to 2.0 equivalents (eq.) with respect to 1 equivalent (eq.) of the methyl ketone derivative (III) from the perspective of suppressing generation of white accretion.

3. Method For Producing Azole Derivative (I)

The method for producing an azole derivative (I) of the present aspect (hereinafter, referred to as "production method 3") will be described. The production method 3 of the present aspect includes the method for producing the oxirane derivative (IV) of the present aspect described above to produce the oxirane derivative (IV), which is an intermediate product of an azole derivative (I), and includes converting the oxirane derivative (IV) obtained by the production method into the azole derivative (I) according to Scheme 3 below (hereinafter, referred to as "Step 3"). By the configuration described above, the azole derivative (I) can be produced at a low cost because the oxirane derivative (IV) can be produced at a low cost.

Since the method for producing the oxirane derivative (IV) is as described above, only Step 3 will be described here. Note that $R^1$, $X^1$, $X^2$, and n in the following Scheme 3 correspond to $R^1$, $X^1$, $X^2$, and n in General Formula (IV) above.

Scheme 3

[Chem. 9]

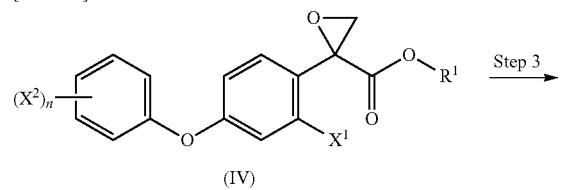

(IV)

-continued

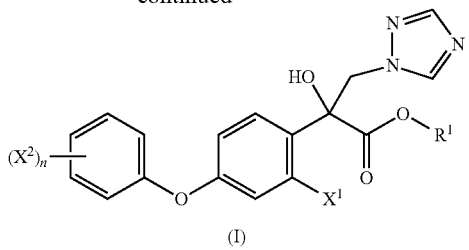

(I)

In Step 3 in the production method 3 of the present aspect, the oxirane derivative (IV) formed in the production method 1 is converted into the azole derivative (I) using 1,2,4-triazole in the presence of an inorganic base.

In Step 3, using 1,2,4-triazole and an inorganic base, azolation is performed while a salt of the 1,2,4-triazole and the inorganic base (e.g., in a case where potassium carbonate is used as the inorganic base, potassium 1,2,4-triazolate) is prepared in the reaction system. As a result, the production efficiency is improved because advance preparation of the salt of the 1,2,4-triazole and the inorganic base is not necessary, which is advantageous for an operator.

Examples of the inorganic base used in Step 3 are same as those described for Step 1. The inorganic base used in Step 3 may be the same as or different from the inorganic base used in Step 1.

The amount of the inorganic base coexisted in the reaction system in Step 3 is preferably from 0.1 to 3.0 equivalents (eq.) with respect to 1 equivalent (eq.) of the oxirane derivative (IV) from the perspective of proceeding the reaction of Step 3.

The amount of 1,2,4-triazole added to the reaction system in Step 3 is preferably from 1.0 to 3.0 equivalents (eq.) with respect to 1 equivalent (eq.) of the oxirane derivative (IV) from the perspective of adequately performing the reaction of Step 3.

Step 3 proceeds in an organic solvent. As the organic solvent, a solvent proceeding the reaction of Step 3 is appropriately selected, and examples of the organic solvent include N,N-dimethylformamide and N,N-dimethylacetamide. The reaction of Step 3 can be performed, for example, at room temperature while stirring is performed or in an oil bath while heating and stirring are performed. As the reaction temperature at this time, for example, the internal temperature is from 40 to 120° C.

The method for converting the oxirane derivative (IV) into the azole derivative (I) is not limited to the method described above and can be performed by a known method (e.g., method described in Patent Document 1). Thus, the production method 3 according to another aspect of the present invention includes the method for producing the oxirane derivative (IV) of the present aspect described above and may convert the oxirane derivative (IV) obtained by the production method into the azole derivative (I) according to a known method (e.g., method described in Patent Document 1).

The present invention is not limited to the above-described embodiments, and various modifications can be made within the scope of the claims, and embodiments obtained by appropriately combining technical means disclosed in different embodiments are also included in the technical scope of the present invention.

Summary

The production method according to the present aspect 1 is a method for producing a compound represented by General Formula (IV) including Step 1, which is converting a compound represented by General Formula (II) into the compound represented by General Formula (IV) using (a) dimethyl sulfide and/or dimethyl sulfoxide and (b) a methyl-LG (an LG is a nucleophilically substitutable leaving group and is selected from the group consisting of a halogen group, an alkoxysulfonyloxy group, an aryloxysulfonyloxy group, an alkylsulfonyloxy group, a haloalkylsulfonyloxy group, and an arylsulfonyloxy group) in the presence of an inorganic base. By this configuration, the oxirane derivative (IV) can be produced without using TMSOB, which is costly.

The production method according to the present aspect 2 preferably includes divided addition of the amounts required for reaction of the (a) and the (b) in Step 1 of converting into the compound represented by General Formula (IV) of the present aspect 1. By the divided addition of the (a) and the (b), reaction is efficiently performed, and thus the used amounts of reagents of the (a) and the (b) can be reduced.

In the production method according to the present aspect 3, the (a) of the present aspect 1 or 2 is preferably both of dimethyl sulfide and dimethyl sulfoxide. In the (a), the used amount of a reagent of the (a) can be reduced by addition of the dimethyl sulfide.

The production method according to the present aspect 4 further includes Step 2, which is converting a compound represented by General Formula (III) into the compound represented by General Formula (II) in any one of the present aspects 1 to 3; and in Step 2, in a solvent containing dimethyl sulfoxide, bromine may be allowed to react with the compound represented by General Formula (III) while a reaction system is heated, and subsequently $R^1$—OH (where $R^1$ is the same as $R^1$ in Formula (IV)) may be allowed to react, and thus the compound represented by General Formula (II) is formed. By this configuration, the ketoester derivative (II) can be produced without using iodine and iodomethane, which are costly.

In the production method according to the present aspect 5, in Step 2 of converting into the compound represented by General Formula (II) in the present aspect 4, in the solvent containing dimethyl sulfoxide, after a reaction system to which bromine is added is heated, the bromine is preferably allowed to react with the compound represented by General Formula (III) by adding the compound represented by General Formula (III), and subsequently $R^1$—OH (where $R^1$ is the same as $R^1$ in Formula (IV)) is preferably allowed to react, and thus the compound represented by General Formula (II) is formed. By addition of the methyl ketone derivative (III) after the reaction system is heated, heat build-up can be suppressed, and thus Step 2 can proceed more safely.

In the production method according to the present aspect 6, Step 2 of converting into the compound represented by General Formula (II) in the present aspect 4 or 5 is performed in the presence of at least one selected from the group consisting of urea, adipic acid dihydrazide, and dibutylhydroxytoluene. By this configuration, generation of the white accretion attached inside the reactor in Step 2 can be suppressed.

The production method according to the present aspect 7 is a method for producing a compound represented by General Formula (I), the method including the method for producing a compound represented by General Formula (IV) according to any one of the present aspects 1 to 6, and Step 3 of converting the compound represented by General Formula (IV) obtained by the production method into the compound represented by General Formula (I) using 1,2,4-triazole in the presence of an inorganic base. By the configuration described above, the production cost of the intermediate product of the azole derivative (I) can be reduced, and thus the production cost of the azole derivative (I) can be reduced.

EXAMPLES

The present invention will now be explained in greater detail through the use of production examples. Moreover, the present invention is not limited to the production examples given below, as long as the gist of the invention is not exceeded.

Synthesis Example 1

Methyl 2-(2-Chloro-4-(4-Chlorophenoxy)Phenyl)-2-Oxiranecarboxylate

Synthesis Example 1-1

After 0.98 g (3.0 mmol) of methyl 2-(2-chloro-4-(4-chlorophenoxy)phenyl)-2-oxoacetate and 4.5 mL of dichloroethane were added to a flask, 2.24 g (16.2 mmol) of potassium carbonate, 1.54 mL (16.2 mmol) of dimethyl sulfate, and 0.58 mL (8.1 mmol) of dimethyl sulfoxide were added, and heated, refluxed, and stirred in an oil bath at 95° C. Two hours after the reaction started, water was added, extraction was performed twice using dichloroethane, and the obtained material was washed with water once. After drying over anhydrous sodium sulfate, the solvent was distilled off, and thus 1.06 g of a yellow liquid crude product was obtained.

The above-mentioned compound in this yellow liquid crude product was quantified by NMR. As a result, the NMR quantified yield of the above-mentioned compound was 61%.

Synthesis Example 1-2

After 12.90 g (purity: 76%; 30 mmol) of crude methyl 2-(2-chloro-4-(4-chlorophenoxy)phenyl)-2-oxoacetate, 14.95 g (108 mmol) of potassium carbonate, and 60 mL of dichloroethane were added in a flask, 3.84 mL (54 mmol) of dimethyl sulfoxide and 10.26 mL (108 mmol) of dimethyl sulfate were divided and added in multiple batches. The reaction was performed in an oil bath at 95° C. while heating and refluxing were performed. Seven and a half hours after the reaction started, water was added to separate the liquid, an aqueous layer was re-extracted once with dichloroethane, and then an organic layer was combined and washed with water twice. After drying over anhydrous sodium sulfate, the solvent was distilled off, and thus 13.07 g of an orange liquid crude product was obtained.

The above-mentioned compound in this orange liquid crude product was quantified by gas chromatography (GC quantification). As a result, the GC quantified yield of the above-mentioned compound was 91%.

Synthesis Example 1-3

After 17.18 g (purity: 76%; 40 mmol) of crude methyl 2-(2-chloro-4-(4-chlorophenoxy)phenyl)-2-oxoacetate, 13.27 g (96 mmol) of potassium carbonate, 1.8 mL (24 mmol) of dimethyl sulfide, and 60 mL of dichloroethane were added in a flask, 3.4 mL (48 mmol) of dimethyl sulfoxide and 7.1 mL (96 mmol) of dimethyl sulfate were divided and added in multiple batches. The reaction was performed in an oil bath at 95° C. while heating and refluxing were performed. Five hours after the reaction started, water was added to separate the liquid, and an organic layer was washed with water twice. After drying over anhydrous sodium sulfate, the solvent was distilled off, and thus 17.50 g of an orange liquid crude product was obtained.

The above-mentioned compound in this orange liquid crude product was quantified by gas chromatography (GC quantification). As a result, the GC quantified yield of the above-mentioned compound was 97%.

Synthesis Example 1-4

After 0.98 g (3.0 mmol) of methyl 2-(2-chloro-4-(4-chlorophenoxy)phenyl)-2-oxoacetate, 3.82 g (18.0 mmol) of potassium phosphate, and 6.0 mL of dichloroethane were added in a flask, 0.85 mL (9.0 mmol) of dimethyl sulfate and 0.32 mL (4.5 mmol) of dimethyl sulfoxide were divided and added in multiple batches. The reaction was performed in an oil bath at 95° C. while heating and refluxing were performed. Seven hours after the reaction started, water was added, extraction was performed twice using dichloroethane, and the obtained material was washed with water once. After drying over anhydrous sodium sulfate, the solvent was distilled off, and thus 1.16 g of a yellow liquid crude product was obtained.

The above-mentioned compound in this yellow liquid crude product was quantified by NMR. As a result, the NMR quantified yield of the above-mentioned compound was 76%.

Synthesis Example 2

Synthesis of Methyl 2-(2-Chloro-4-(4-Chlorophenoxy)Phenyl)-2-Oxoacetate

Synthesis Example 2-1

In a flask, 28.11 g (0.10 mol) of 2'-chloro-4'-(4-chlorophenoxy)acetophenone, 50 mL of dimethyl sulfoxide, and 45 mL of dichloroethane were added, dissolved, and cooled in an ice bath, and then 19.32 g (0.12 mol) of bromine was added by a dropping funnel, washed with 5 mL of dichloroethane, and heated and stirred in an oil bath in a manner that the internal temperature was 70° C. After 1 hour, low boiling point substances were distilled off, and 50 mL of toluene and 50 mL of methanol were added and heated and refluxed. After 1 hour, 50 mL of toluene was added to separate the bottom layer of the solution, and the bottom layer was re-extracted with toluene once. The top layer and the re-extracted toluene were combined and washed with a saturated sodium bicarbonate solution once, washed with water once, and washed with saturated brine solution once. After drying over anhydrous sodium sulfate, the solvent was distilled off, and thus 30.83 g of an orange liquid crude product was obtained.

The above-mentioned compound in this orange liquid crude product was quantified by gas chromatography (GC quantification). As a result, the GC quantified yield of the above-mentioned compound was 83%.

Synthesis Example 2-2

After 100 mL of dichloroethane was added to a flask, 38.36 g (0.24 mol) of bromine was added by a dropping funnel and stirred. After the reactor was cooled in a water bath, 28.4 mL of dimethyl sulfoxide was added by a dropping funnel. After heating was performed in an oil bath to make the internal temperature 70° C., 85.2 mL of dimethyl sulfoxide solution of 56.23 g (0.20 mol) 2'-chloro-4'-(4-chlorophenoxy)acetophenone was added by a dropping funnel. One hour after completion of the dropwise addition, 7.1 mL of dimethyl sulfoxide was added. Further after 1 hour, low boiling point substances were distilled off, and 100 mL of toluene and 100 mL of methanol were added and heated and refluxed. After 2 hours, 100 mL of toluene was added to separate the bottom layer of the solution, and the bottom layer was re-extracted with toluene once. The top layer and the re-extracted toluene were combined and washed with a saturated sodium bicarbonate solution once, and washed with water twice. The solvent was distilled off, and thus 59.29 g of an orange liquid crude product was obtained.

The above-mentioned compound in this orange liquid crude product was quantified by gas chromatography (GC quantification). As a result, the GC quantified yield of the above-mentioned compound was 77%.

Synthesis Example 2-3

After 18.01 g (0.30 mol) of urea and 468 mL of dichloroethane were added in a flask, 191.80 g (1.20 mol) of bromine was added in a dropping funnel and stirred. After the reactor was cooled in a water bath, a mixed solution of 156.26 g (2.00 mol) of dimethyl sulfoxide and 25 mL of dichloroethane was added by a dropping funnel. After stepwise heating was performed in an oil bath to make the internal temperature 70° C. while the internal temperature was monitored, 468.77 g (6.00 mol) of dimethyl sulfoxide solution of 283.11 g (1.00 mol) 2'-chloro-4'-(4-chlorophenoxy)acetophenone was added by a dropping funnel. One hour after completion of the dropwise addition, 39.07 g (0.50 mol) of dimethyl sulfoxide and 6 mL of dichloroethane were added. Further after 1 hour, low boiling point substances were distilled off, and 500 mL of toluene and 500 mL of methanol were added and heated and refluxed. After 3 hours, 500 mL of toluene was added to separate the bottom layer of the solution, and the bottom layer was re-extracted with toluene once. The top layer and the re-extracted toluene were combined and washed with water once, washed with a 5% sodium bicarbonate solution once, and washed with water once. 1671.78 g of toluene solution of the target product was obtained as an orange liquid.

The above-mentioned compound in this orange liquid was quantified by gas chromatography (GC quantification). As a result, the GC quantified yield of the above-mentioned compound was 79%.

Furthermore, Synthesis Example 2-3 was able to suppress 95% or more of generation of white accretion attached inside the reactor compared to those of synthesis Example 2-1 and Synthesis Example 2-2.

Synthesis Example 2-4

After 500 mL of dichloroethane and 191.79 g (1.20 mol) of bromine were added in a flask, heating and stirring were performed in an oil bath until the internal temperature became 65° C., and then 156.28 g (2.00 mol) of dimethyl sulfoxide solution of 18.02 g (0.30 mol) of urea was added by a dropping funnel. Then, 351.59 g (4.50 mol) of dimethyl sulfoxide solution of 283.68 g (purity: 99.1%; 1.00 mol) of 2'-chloro-4'-(4-chlorophenoxy)acetophenone was added by a dropping funnel. One hour after completion of the dropwise addition, 39.13 g (0.50 mol) of dimethyl sulfoxide was added. Further after 2 hours, low boiling point substances were distilled off, and 500 mL of toluene and 500 mL of methanol were added and heated and refluxed. After 7 hours, the bottom layer of the solution was separated, and the bottom layer was re-extracted with toluene once. The top layer and the re-extracted toluene were combined and washed with water for three times. 1261.67 g of toluene solution of the target product was obtained as an orange liquid.

The above-mentioned compound in this orange liquid was quantified by gas chromatography (GC quantification). As a result, the GC quantified yield of the above-mentioned compound was 84%.

Synthesis Example 3

Synthesis of Methyl 2-(2-Chloro-4-(4-Chlorophenoxy)Phenyl)-2-Hydroxy-3-(1H-1,2,4-Triazol-1-yl) Propionate After 152.35 g (purity: 74%; 0.33 mol) of crude methyl 2-(2-chloro-4-(4-chlorophenoxy)phenyl)-2-oxiranecarboxylate and 154.12 g of N,N-dimethylacetamide were added in a flask, 34.64 g (0.50 mol) of 1,2,4-triazole and 23.09 g (0.17 mol) of potassium carbonate were added, and heated and stirred in an oil bath at 50° C. After 0.75 hours, the internal temperature was raised to 60° C. After 5 hours, cooling to room temperature was performed, and among 363.71 g of the reaction solution, 111.95 g (0.10 mol equivalent) was transferred into a 500 mL cylindrical separable flask, 50 mL of toluene and 40 mL of water were added, and then 30 mg of seed crystal of the above-mentioned compound was added. After 30 minutes, 160 mL of water was added dropwise and stirred at room temperature for 30 minutes, cooling was gradually performed over 30 minutes using a cyclohexane bath at 6° C., and stirring was continued for 3 hours. Then, the crude liquid was vacuum-filtered and washed by using 50 mL of water and 25 mL of toluene. The filtered material was dried under a reduced pressure using a vacuum specimen dryer, and thus 39.09 g of a target white solid crude product was obtained.

The above-mentioned compound in this white solid crude product was quantified by high-performance liquid chromatography (HPLC quantification). As a result, the HPLC quantified yield of the above-mentioned compound was 78%. Furthermore, triazol-1-yl:triazol-4-yl was 85:15.

36.6 g of the white solid crude product was subjected to hot filtration at 100° C. while 164.8 g of toluene was used in appropriately divided batches. In a flask, 189 g of the filtrate was added, the temperature was raised to 100° C. in an oil bath, and after the inner temperature reached 100° C., heating and stirring were performed for 10 minutes. Then, cooling was performed to 92° C. at the rate of 15° C./h. After reaching 92° C., 159 mg of seed crystal of the above-mentioned compound was added, and then stirring was performed at 92° C. for 30 minutes. Then, cooling was performed to 75° C. at 6° C./h, from 75° C. to 55° C. at 10° C./h, and from 55° C. to 5° C. at 30° C./h, and after reaching 5° C., stirring was continued for 2 hours. The crude liquid was vacuum-filtered and washed by using 11.3 g of cold toluene. The filtered material was dried under a reduced pressure using a vacuum specimen dryer, and thus 31.2 g of a target white solid was obtained.

The above-mentioned compound in this white solid crude product was quantified by high-performance liquid chromatography (HPLC quantification). As a result, the HPLC quantified recovery rate of the above-mentioned compound was 94.6%. At this time, triazol-1-yl:triazol-4-yl was 95:5.

Powder X-ray diffraction data of the triazol-1-yl (A), the triazol-4-yl (B), and the mixture (C) including the triazol-1-yl:triazol-4-yl of 95:5 was recorded at room temperature by irradiation of germanium-CuKα1 radiation ($\lambda$=1.5406 Å). 2θ Scan of 5°≤2θ≤35° (step size: 0.03°) was performed at room temperature by using a one-dimensional position sensitive detector.

The powder X-ray diffraction patterns of the triazol-1-yl (A), the triazol-4-yl (B), and the mixture (C) including the triazol-1-yl:triazol-4-yl of 95:5 are respectively shown in FIGS. 1 to 3. Furthermore, 2θ values of the powder X-ray diffraction patterns are shown in Table 1 below.

TABLE 1

| A | B | C |
|---|---|---|
| 5.97 | 5.26 | 5.89 |
| 11.91 | 10.62 | 11.64 |
| 12.78 | 12.75 | 11.80 |
| 13.48 | 13.64 | 12.70 |
| 16.09 | 13.90 | 13.38 |
| 16.77 | 15.19 | 15.35 |
| 17.27 | 15.64 | 16.00 |
| 19.00 | 16.71 | 16.66 |
| 19.63 | 17.34 | 17.12 |
| 20.39 | 17.58 | 18.92 |
| 20.89 | 18.16 | 19.52 |
| 22.02 | 18.40 | 20.26 |
| 23.46 | 18.87 | 20.81 |
| 23.83 | 19.13 | 23.38 |
| 24.40 | 20.02 | 23.75 |
| 24.61 | 20.86 | 24.28 |
| 24.80 | 22.20 | 24.54 |
| 26.22 | 23.12 | 24.72 |
| 26.82 | 24.28 | 26.14 |
| 27.27 | 25.28 | 26.75 |
| 29.45 | 26.14 | 27.19 |
| 29.95 | 27.90 | 29.35 |
| 31.42 | 29.56 | 29.84 |
| 31.87 | 29.92 | 31.34 |
| 32.50 | 31.50 | 31.74 |
|  | 32.13 | 32.42 |
|  | 32.86 | 33.92 |
|  | 33.15 | 34.41 |
|  | 34.89 |  |

INDUSTRIAL APPLICABILITY

An embodiment of the present invention can be utilized as a method for producing an intermediate product for synthesizing an azole derivative useful as an agricultural or horticultural chemical.

The invention claimed is:

1. A method for producing a compound represented by General Formula (IV):

[Chem. 1]

where in General Formula (IV), $R^1$ is a $C_1$-$C_6$-alkyl group;

$X^1$ is a halogen group, a $C_1$-$C_4$-haloalkyl group, or a $C_1$-$C_4$-haloalkoxy group;

$X^2$ is a halogen group, a $C_1$-$C_4$-haloalkyl group, or a $C_1$-$C_4$-haloalkoxy group; and n is 1, 2, or 3;

the method comprising converting a compound represented by General Formula (III) into a compound represented by General Formula (II):

[Chem. 2]

where in Formula (II), $R^1$, $X^1$, $X^2$, and n are respectively the same as $R^1$, $X^1$, $X^2$ and n in Formula (IV),

[Chem. 3]

where in Formula (III), $X^1$, $X^2$, and n are respectively the same as $X^1$, $X^2$, and n in Formula (IV), wherein, in the converting step, in a solvent containing dimethyl sulfoxide, bromine is allowed to react with the compound represented by General Formula (III) while a reaction system is heated, and subsequently $R^1$—OH (where $R^1$ is the same as $R^1$ in Formula (IV)) is allowed to react, and thus the compound represented by General Formula (II) is formed, wherein the step of converting into the compound represented by General Formula (II) is performed in the presence of at least one selected from the group consisting of urea, adipic acid dihydrazide, and dibutylhydroxytoluene, the method further comprising converting thea compound represented by General Formula (II) into the compound represented by General Formula (IV) using:

(a) dimethyl sulfide and/or dimethyl sulfoxide, and (b) a methyl-LG, where LG is a nucleophilically substitutable leaving group and is selected from the group consisting of a halogen group, an alkoxysulfonyloxy group, an aryloxysulfonyloxy group, an alkylsulfonyloxy group, a haloalkylsulfonyloxy group, and an arylsulfonyloxy group in the presence of an inorganic base.

2. The method according to claim 1, wherein, in the step of converting into the compound represented by General Formula (IV), amounts required for a reaction of the (a) and the (b) are divided and added in multiple batches.

3. The method according to claim 1, wherein the (a) is dimethyl sulfide and dimethyl sulfoxide both.

4. The method according to claim 1, wherein, in the step of converting into the compound represented by General Formula (II), in the solvent containing dimethyl sulfoxide, after a reaction system to which bromine is added is heated, the bromine is allowed to react with the compound represented by General Formula (III) by adding the compound represented by General Formula (III), and subsequently $R^1$—OH (where $R^1$ is the same as $R^1$ in Formula (IV)) is allowed to react, and thus the compound represented by General Formula (II) is formed.

5. A method for producing a compound represented by General Formula (I), comprising the method for producing the compound represented by General Formula (IV) according to claim 1, and
   converting the compound represented by General Formula (IV) obtained by the method into the compound represented by General Formula (I) using 1,2,4-triazole in the presence of an inorganic base:

[Chem. 4]

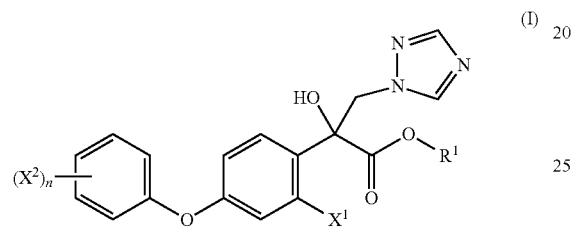

where $R^1$, $X^1$, $X^2$, and n in Formula (I) are respectively the same as $R^1$, $X^1$, $X^2$, and n in Formula (IV).

* * * * *